(12) United States Patent
Greenhalgh et al.

(10) Patent No.: US 12,064,334 B2
(45) Date of Patent: *Aug. 20, 2024

(54) REINFORCED ORTHOPEDIC DEVICES

(71) Applicant: Tela Bio, Inc, Malvern, PA (US)

(72) Inventors: E. Skott Greenhalgh, Gladwyne, PA (US); Antony Koblish, Malvern, PA (US)

(73) Assignee: Tela Bio, Inc., Malvern, PA (US)

( * ) Notice: Subject to any disclaimer, the term of this patent is extended or adjusted under 35 U.S.C. 154(b) by 550 days.

This patent is subject to a terminal disclaimer.

(21) Appl. No.: 16/893,296

(22) Filed: Jun. 4, 2020

(65) Prior Publication Data

US 2020/0297476 A1 Sep. 24, 2020

Related U.S. Application Data

(63) Continuation of application No. 15/272,389, filed on Sep. 21, 2016, now Pat. No. 10,675,141.

(60) Provisional application No. 62/221,602, filed on Sep. 21, 2015.

(51) Int. Cl.
*A61F 2/08* (2006.01)

(52) U.S. Cl.
CPC .............. *A61F 2/08* (2013.01); *A61F 2/0811* (2013.01); *A61F 2002/0858* (2013.01); *A61F 2002/087* (2013.01)

(58) Field of Classification Search
CPC .. A61F 2/08; A61F 2/0811; A61F 2002/0858; A61F 2002/087
See application file for complete search history.

(56) References Cited

U.S. PATENT DOCUMENTS

| | | | |
|---|---|---|---|
| 5,683,400 A | 11/1997 | Mcguire | |
| 5,707,395 A | 1/1998 | Li | |
| 6,371,985 B1 | 4/2002 | Goldberg | |
| 10,675,141 B2 | 6/2020 | Greenhalgh et al. | |
| 2001/0020188 A1 | 9/2001 | Sander | |
| 2006/0229722 A1 | 10/2006 | Bianchi et al. | |
| 2009/0018655 A1 | 1/2009 | Brunelle et al. | |
| 2010/0063599 A1 | 3/2010 | Brunelle et al. | |
| 2010/0249929 A1 | 9/2010 | Kurz et al. | |
| 2011/0196490 A1 | 8/2011 | Gadikota et al. | |
| 2013/0116799 A1* | 5/2013 | Derwin | A61L 27/38 623/23.72 |
| 2017/0079769 A1 | 3/2017 | Greenhalgh et al. | |

FOREIGN PATENT DOCUMENTS

WO  WO 2003/082363  10/2003

OTHER PUBLICATIONS

Franklin, I.J. et al., "Uptake of Tetracycline by Aortic Aneurysm Wall and Its Effect on Inflammation and Proteolysis," *Brit. J. Surger*, 86(6):771-775, 1999.

(Continued)

*Primary Examiner* — Marcia L Watkins
(74) *Attorney, Agent, or Firm* — Levine Bagade Han LLP

(57) ABSTRACT

Implantable tensile load-bearing grafts having synthetic components stitched through biological components are disclosed. The synthetic components can be biodegradable and/or non-biodegradable and of differing tensile strengths from each other and the biological component. Methods of making the grafts are also disclosed.

21 Claims, 13 Drawing Sheets

(56) References Cited

OTHER PUBLICATIONS

Pyo, R. et al., "Targeted Gene Disruption of Matrix Metalloproteinase-9 (Gelatinase B) Suppresses Development of Experimental Abdominal Aortic Aneurysms," *J. Clinical Investigation*, 105(11):1641-1649, Jun. 2000.

Tambiah, J. et al., "Provocation of Experimental Aortic Inflammation Mediators and Chlamydia Pneumoniae," *Brit., J. Surgery*, 88(7):935-940, Feb. 2001.

Walton, L.J. et al., "Inhibition of Prostoglandin E2 Synthesis in Abdominal Aortic Aneurysms," *Circulation*, 48-54, Jul. 6, 1999.

Xu, Q. et al., "Sp1 Increases Expression of Cyclooxygenase-2 in Hypoxic Vascular Endothelium," *J. Biological Chemistry*, 275(32):24583-24589, Aug. 2000.

\* cited by examiner

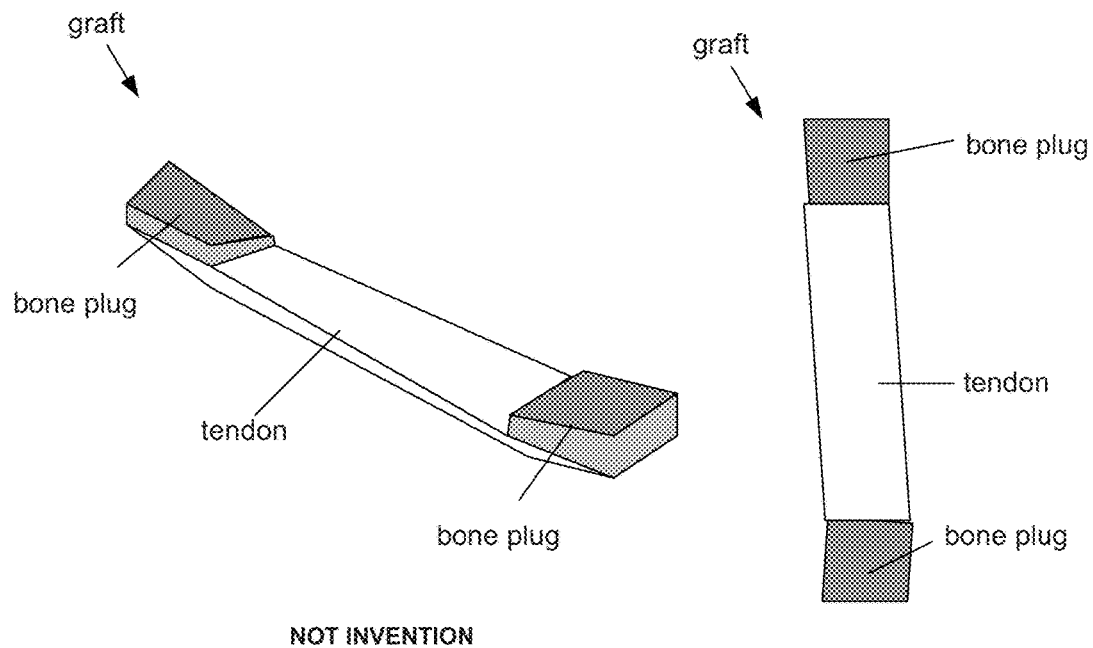
Fig. 1a NOT INVENTION
Fig. 1b NOT INVENTION
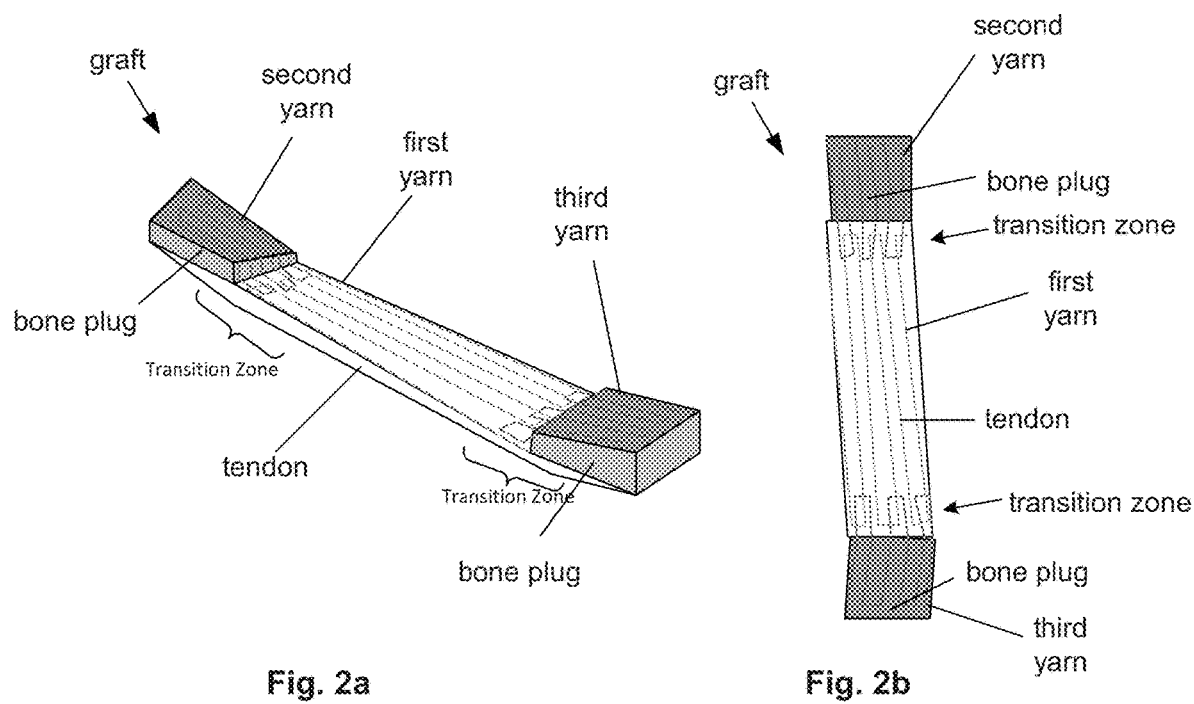
Fig. 2a
Fig. 2b

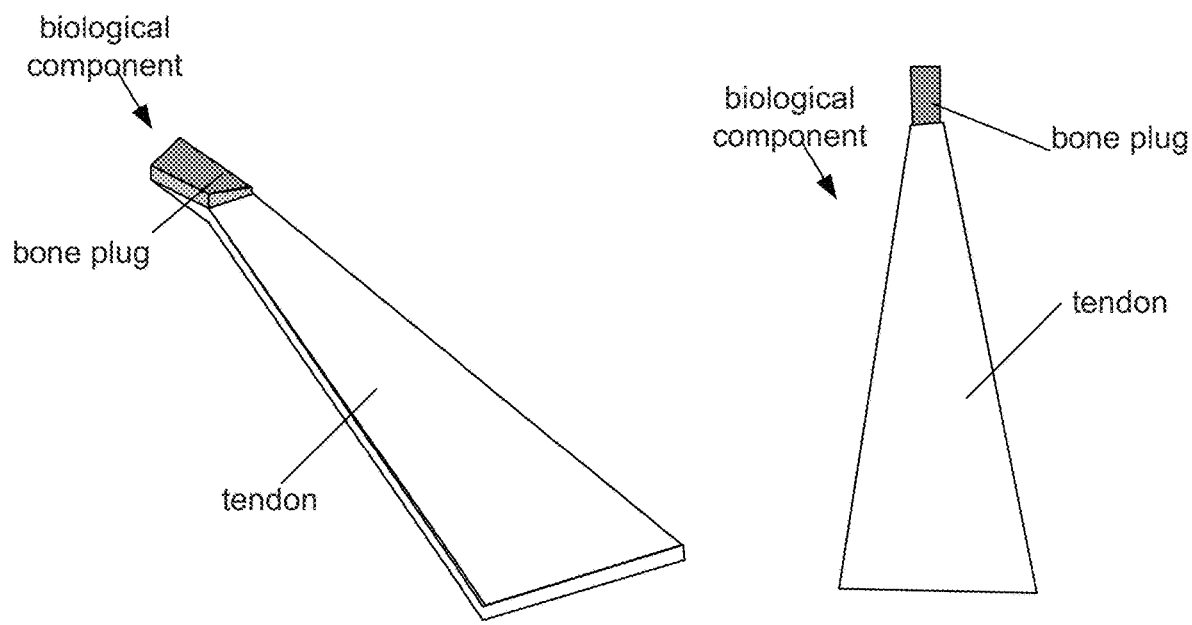
Fig. 4a
Fig. 4b
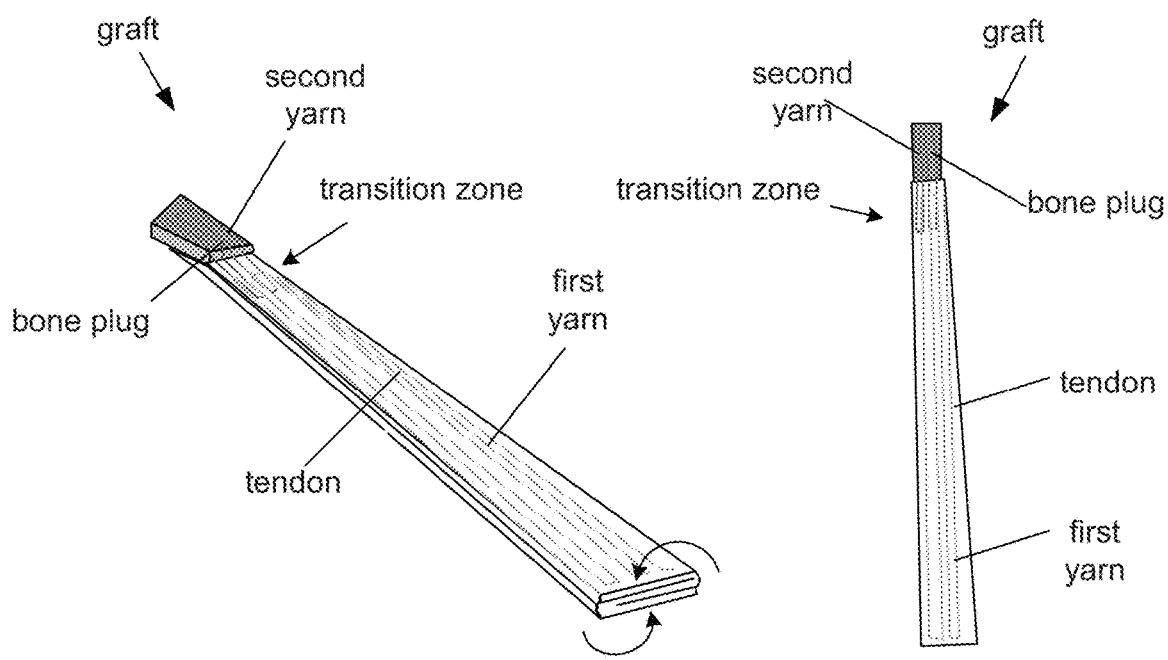
Fig. 5a
Fig. 5b

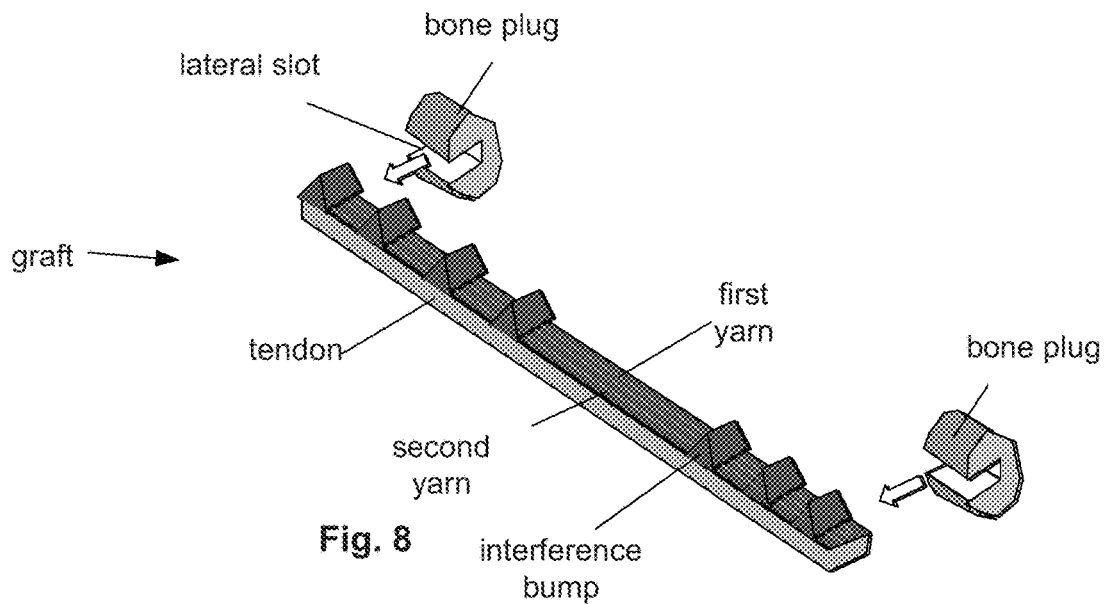
Fig. 8
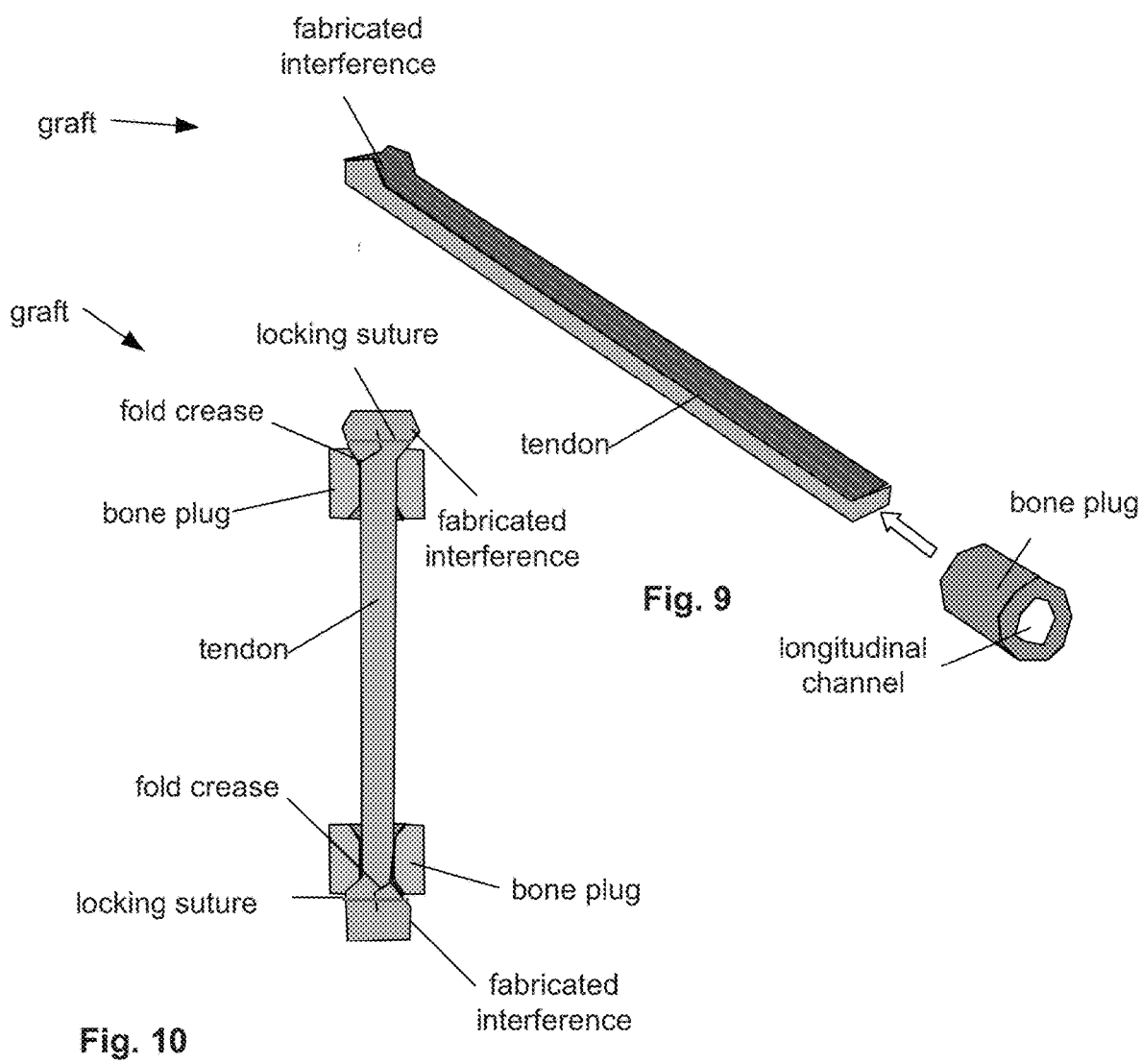
Fig. 9
Fig. 10

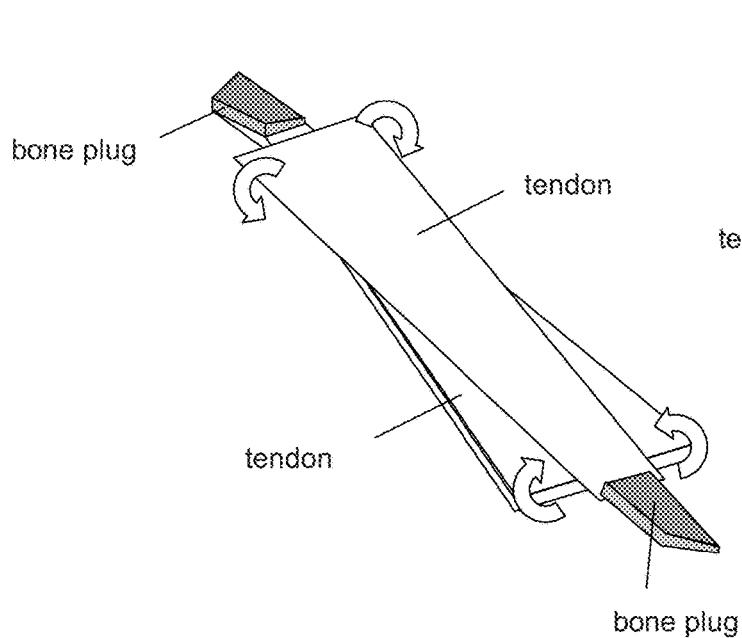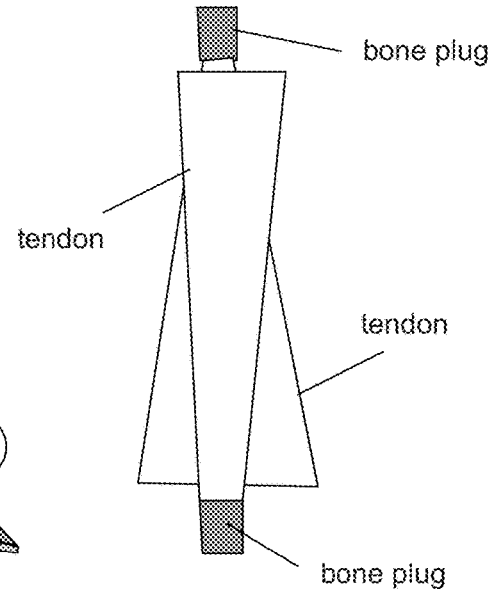
Fig. 13a  Fig. 13b
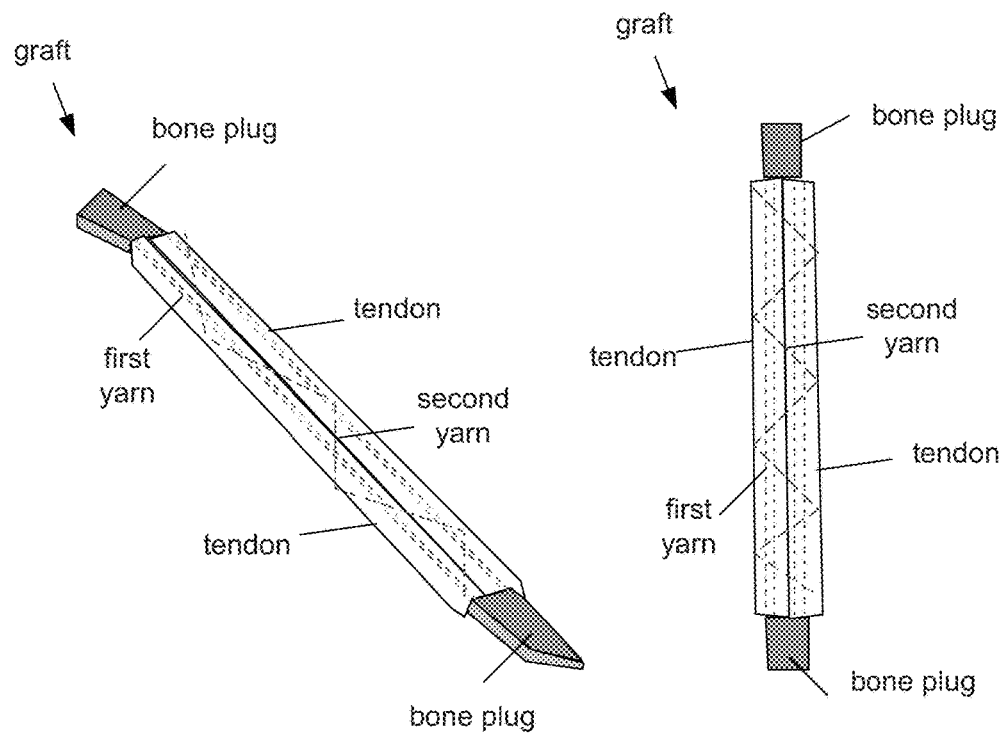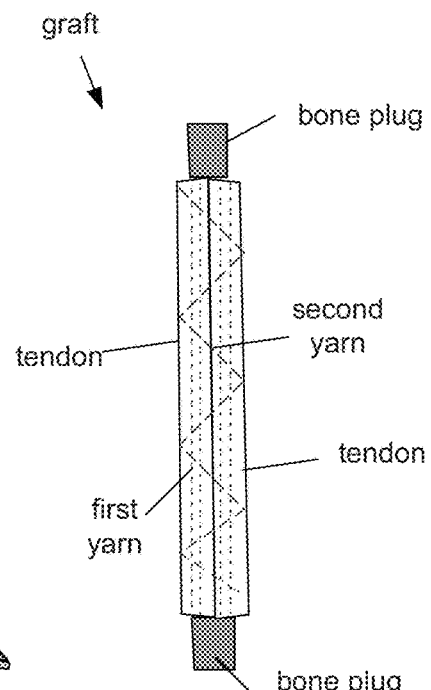
Fig. 14a  Fig. 14b

US 12,064,334 B2

REINFORCED ORTHOPEDIC DEVICES

CROSS-REFERENCE TO RELATED APPLICATIONS

This application is a continuation of U.S. patent application Ser. No. 15/272,389 filed Sep. 21, 2016 (now U.S. Pat. No. 10,675,141 issued Jun. 9, 2020), which claims the benefit of priority to U.S. Provisional Application No. 62/221,602 filed Sep. 21, 2015, each of which is incorporated herein by reference in its entirety for all purposes.

BACKGROUND

1) Technical Field

This disclosure relates generally to implantable tensile load-bearing grafts having synthetic components stitched through biological components.

2) Description of the Related Art

Reconstruction of a ruptured anterior cruciate ligament (ACL) is one of the most common procedures performed by sports medicine surgeons today. Few would dispute the importance of the ACL to knee stability and function. Anatomic intra-articular reconstruction is common for ACL patients or those with function disability due to acute or chronic ACL deficiency.

However, some in the field previously stated that the ACL did not need repair if the associated meniscal and capsular pathology was appropriately addressed. They failed to recognize the importance of the ACL as the primary restraint to anterior translation of the tibia and the prevalence of isolated ACL rupture.

Various techniques address the problem of ACL rupture. Primary repair and substituting the ACL with extra-articular reconstructions using local structures are known techniques but considered outdated by many. A common repair procedure passes grafts through a tibial tunnel and intra-articularly. The proximal end of the graft is then passed through the condyle notch on the femur and secured on the lateral aspect of the femur or through a tunnel in the femur. Some procedures include a double-bundle: implanting two grafts to attempt to mechanically replicate the force loading of the ACL.

Soft-tissue grafts and synthetic prosthetic replacements are used for ACL repair. Common tissue replacements include fascia lata grafts, hamstring grafts, and quadriceps or patellar tendon (also referred to as patellar ligament) grafts.

FIGS. 1a and 1b illustrate a variation of an ACL graft made from patellar tendon. The graft has a tendon length in the middle of the graft and bone plugs at each terminal end of the graft. The bone can be integral with the tendon, having been the natural bone at the ends of the tendon before excising the graft from the host location, or can be attached to the tendon after the tendon is removed from the host location. The graft is shown having a generally rectangular cross-section, but circular cross-sectional (i.e., cylindrical) grafts are also used.

Synthetic ACL replacements include structures made from polyethylene, such as the Polyflex, porous PTFE (Teflon) grafts, such as the Proplast, and grafts using carbon fiber, Gore-Tex, Dacron, and polypropylene. The polypropylene graft known as the Ligament Augmentation Device (LAD) was the only one to gain widespread use. These synthetics often failed as they tended to stretch or fragment over time.

Biological graft strength varies with time after implant. Natural stressing of the graft is beneficial for long-term strengthening of the graft, but the failure stress of biological grafts decreases after implantation and before the strength of the graft increases. Accordingly, failure of biological grafts may occur during rigorous post-replacement physical therapy intended to strengthen the graft. On the other hand, synthetic grafts start strong after implantation, but are known to sometimes fail due to long-term issues such as stretching or fragmentation.

Accordingly, it is desired to provide an ACL graft that has the long-term strength and biocompatibility of a biological graft with the short-term strength of a synthetic graft.

SUMMARY

An implantable orthopedic device, such as a graft, for implantation as a tensile load bearing element in a target site is disclosed. The device can have a biological component and a first synthetic component. The biological component can have a longitudinal axis. The biological component can be configured to sustain a first portion of the tensile load. The biological component can have a soft tissue and/or a hard tissue. The first synthetic component can be configured to sustain a second portion of the tensile load. The first synthetic component can extend through the biological component. The first synthetic component may not extend beyond the longitudinal extent of the biological component.

At least a length of the first synthetic component can be stitched through the biological component. At least a length of the first synthetic component can form a lockstitch through the biological component.

The device can have a second synthetic component configured to sustain a third portion of the tensile load. The second synthetic component can extend through the biological component. The second synthetic element can overlap with the first synthetic element in a longitudinal direction of the device. The second synthetic component can have a non-biodegradable material. The first synthetic component can have a biodegradable material.

The first synthetic component can have one or more yarns, threads (e.g., multifilament or monofilament), fibers, leaders, wires, cords, or combinations thereof. The soft tissue can have or be a ligament, a tendon, a muscle, or combinations thereof. The hard tissue can have or be a bone, a first bone plug at a first terminal end of the device and a second bone plug at a second terminal end of the device, or combinations thereof.

An implantable orthopedic device, such as a graft, for implantation as a tensile load bearing element in a target site is further disclosed. The device can have a biological component and a first synthetic component. The biological component can have a longitudinal axis and be configured to sustain a first portion of the tensile load. The biological component can have a soft tissue and/or a hard tissue.

The first synthetic component can be configured to sustain a second portion of the tensile load. The first synthetic component can extend through the biological component and be biodegradable.

Furthermore, an implantable orthopedic device, such as a graft, for implantation as a tensile load bearing element in a target site is disclosed. The device can have a biological component, a first synthetic component, and a second synthetic component. The biological component can have a longitudinal axis and be configured to sustain a first portion of the tensile load. The biological component can have a soft tissue and/or a hard tissue.

The first synthetic component can be configured to sustain a second portion of the tensile load. The first synthetic component can extend through the biological component. The first synthetic material can have a first strength per cross-sectional area.

The second synthetic component can be configured to sustain a third portion of the tensile load. The second synthetic component can extend through the biological component. The second synthetic material can have a second strength per cross-sectional area. The second strength per cross-sectional area can be greater than the first strength per cross-sectional area.

The first and second strength per cross-sectional area can have or be a first and second modulus of elasticity, respectively. The first and second strength per cross-sectional area can have or be a first and second yield stress, respectively. The first and second strength per cross-sectional area can have a first and second failure stress, and wherein the second strength per cross-sectional area comprises a second failure stress, respectively.

A method for making an implantable orthopedic device is disclosed. The method can include inserting a first synthetic element through a biological component. The biological component can have a soft tissue. The first synthetic element can be inserted through the soft tissue. The first synthetic element can have a first yarn. The method can further include inserting a second synthetic element through the soft tissue. The second synthetic element can be stronger than the first synthetic element.

The second synthetic element can overlap with the first synthetic element in a longitudinal direction of the device. The inserting of the first synthetic element can include forming a lockstitch with the first synthetic element. The second synthetic element can have a second yarn.

The method can include folding the biological component over onto itself. The folding can include forming a pocket within the biological component. The method can include placing an attachment element in the pocket.

The method can include creating a bone tunnel, and attaching an anchor to the attachment element. The anchor can have an endobutton outside of the bone tunnel.

The method can include folding the biological component over onto itself at a fold and attaching a bone plug to the fold.

Yet another method for making an implantable orthopedic device is disclosed. The method can include inserting a first synthetic element through a biological component having soft tissue. The first synthetic element can be inserted through the soft tissue. The first synthetic element can have a first yarn. The method can include forming with and/or attaching an interference element to the biological component. The method can include attaching a bone plug to the soft tissue. The bone plug can abut the interference element.

The method can include inserting a second synthetic element through the bone plug and the soft tissue. The second synthetic element can be stronger than the first synthetic element.

The interference element can have an interference bump attached to the soft tissue. The interference element can have a fold of the soft tissue.

An implantable orthopedic device is disclosed that can have a bone plug, a first yarn; and a second yarn. The first yarn can be stitched through the bone plug in a first stitching orientation. The second yarn can be stitched through the bone plug in a second stitching orientation. The first stitching orientation can be non-parallel to the second stitching orientation. The device can have a soft tissue attached to the bone plug. The first stitching orientation can be at a right angle to the second stitching orientation.

BRIEF DESCRIPTION OF THE DRAWINGS

FIGS. 1a and 1b are isometric and side schematic views, respectively, of a known patellar tendon graft, not the invention.

FIGS. 2a and 2b are isometric and side schematic views, respectively, of a variation of the graft.

FIGS. 4a through 7b schematically illustrate a variation of a method for making the graft. FIGS. 4a, 5a, 6a, and 7a are isometric views, and FIGS. 4b, 5b, 6b, and 7b are side views of the respectively numbered isometric views.

FIG. 8 is a perspective schematic view of a variation of a method for assembling the graft.

FIG. 9 is a perspective schematic view of a variation of a method for assembling the graft.

FIG. 10 is a cross-sectional view of a variation of the assembled graft of FIG. 9.

FIGS. 13a through 15b schematically illustrate a variation a method for making the graft. FIGS. 13a, 14a, and 15a are isometric views, and FIGS. 13b, 14b, and 15b are side views of the respectively numbered isometric views.

FIGS. 16 through 19b schematically illustrate a variation of a method for making the graft. FIGS. 19a and 19b are schematic isometric and side views, respectively, of the particular variation of the graft.

FIGS. 25a through 26b schematically illustrate a variation a method for making the graft. FIGS. 25a and 26a are isometric views, and FIGS. 25b and 26b are side views of the respectively numbered isometric views.

DETAILED DESCRIPTION

Figure 3A:
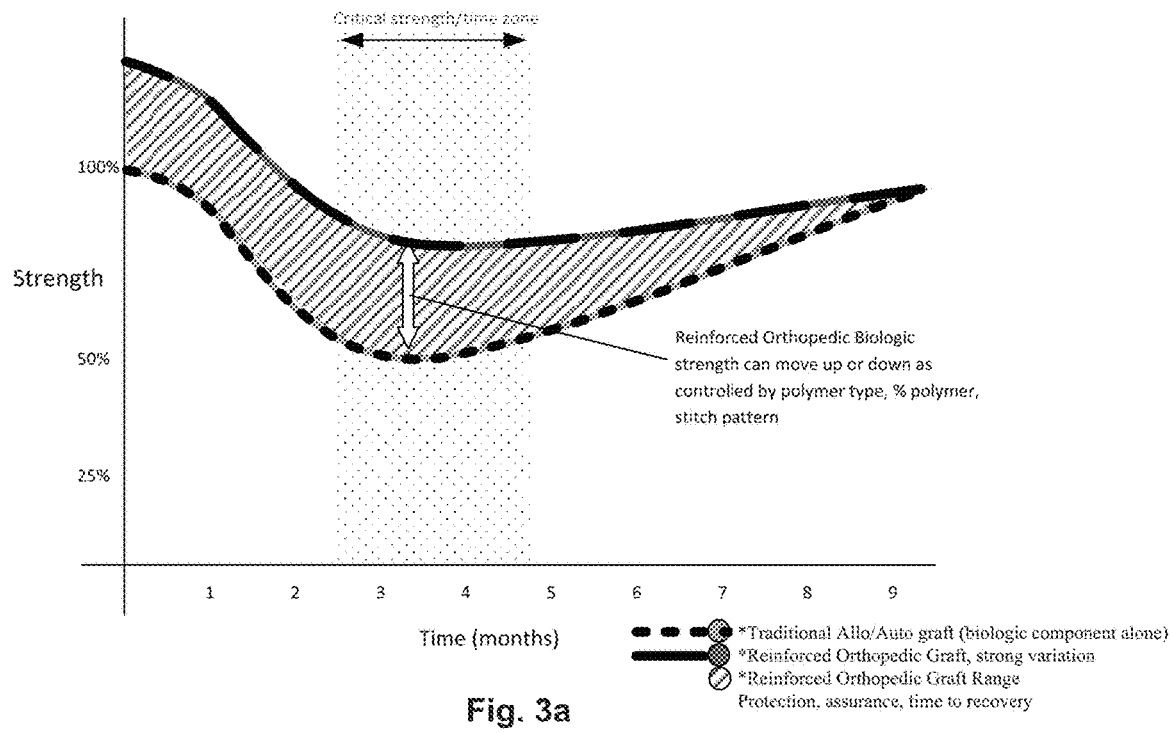
FIG. 3a is a strength vs. time graph of variations of the graft with a biodegradable synthetic component and an exemplary traditional biologic allograft or autograft graft.

FIGS. 2a and 2b illustrate that a device, such as a synthetically reinforced orthopedic graft (e.g., an ACL graft), can have a composite intermingling, interweaving, interstitching, innerlacing, comingling, blending, merging, or combinations thereof, of one or more a natural biologic components and one or more synthetic components.

The graft can be used for tendon or ligament replacement, for example, in the knees (e.g., ACL, PCL, MCL, LCL), ankles (e.g., lateral ankle ligament), shoulder (e.g., GHL, CAL, CCL, THL), spine (e.g., spinal ligament), or combinations thereof.

The biologic component can be a biologic graft, such as a patellar tendon graft, as shown in FIGS. 1a and 1b, other biologic graft listed herein (e.g., fascia lata grafts, hamstring grafts, and quadriceps grafts), or combinations thereof. The biological component can have soft (e.g., fascia membrane, ligament, tendon, muscle, or combinations thereof), hard (e.g., bone) tissue, or combinations thereof. Biologic component can be an allograft, xenograft, autograft, or combinations thereof.

The biological components can be near net shape, partial net shape, assembled, or combinations thereof.

The near net shape can, for example, be a patellar-tendon (e.g., bone plug-tendon-bone plug) source graft, such as shown in FIGS. 1a through 2b. The final part shape or geometry of the near net shape can be defined by the natural geometry of the original source of the biological component.

The partial net shape can, for example, be an Achilles tendon (soft tissue connected to bone on one end) graft, such as shown in FIGS. 4a through 7b. The final part shape of geometry of the partial net shape can be defined by modification to the original source soft tissue element (tendon, ligament, ECM) of the biological component.

The assembled biological component can have a final shape created by a surgeon or engineers before or during a surgical procedure by assembling hard (e.g., bone) and soft (e.g., tendon, ligament, ECM) components into a singular structure of the biological component, such as shown in FIGS. 8-10. For example, the assembled biological component can be assembled from bone pieces (e.g., plugs, wedges, struts, cortical, cancellous, composite of cortical and cancellous, or combinations thereof), soft tissue (e.g., semitendinosus, peroneus longus tendon, gracilis tendon, anterior or anterior tibialis tendon, or combinations thereof), synthetic component and/or other adhesive element, such as by sewing two smaller or thinner autografts or allografts together, for example sewing a first patellar tendon to a second patella tendon, end to end.

The synthetic component can be made from a polymer, metal, a natural material such as collagen, cat gut, silk, HA, cytosan, or combinations thereof, Can be biodegradable (e.g., hydrolytic or pyrolytic), or non-biodegradable. The synthetic component can be one or more yarns, threads (e.g., multifilament or monofilament), fibers, leaders, wires, cords, or combinations thereof. The synthetic component can be a thread. The synthetic element can be inserted through, around, between, inside, or combinations thereof, the hard and/or soft tissue of the biologic component.

The synthetic component can be configured to bear tensile load when the biological component is under a tensile load. The synthetic components can structurally reinforce the biologic component, for example, when tensile loads are applied to the graft.

The graft can have a first synthetic component having a first yarn stitched through the tendon. The graft can have a second synthetic component having a second yarn stitched through a proximal bone plug and the proximal end of the tendon. The graft can have a third synthetic component having a third yarn stitched through a distal bone plug and the distal end of the tendon.

The first, second, and third yarns can all have the same or different diameters or combinations thereof. For example, the second and third yarns can have the same diameter which can be larger than the diameter of the first yarn.

The first, second, and third yarns can all be made from the same or different materials. For example, the second and third yarns can be made from a non-biodegradable materials, and the first yarn can be made from a biodegradable material. Any or all of the yarns can be completely biodegradable or bioabsorbable, or non-biodegradable or non-bioabsorbable.

For example, the second and third yarns (and/or the first yarn) can be multifilament yarns, from about 80 to about 1000 denier, and made from PET, PP, or UHMWPE with a twist, can be braided, and can be inserted (e.g., sewn) and interwoven (e.g., lockstitched) through the bone and tendon.

Also for example, the first yarn (and/or second and/or third yarns) can be made from PGA, PLLA, PLA, PDI, PCL, inserted (e.g., sewn) and interwoven (e.g., lockstitched) through the tendon, and can the compliance or amount of stretch until yield can be the same or less than that of the substrate tissue (e.g., tendon), for example backstopping the tendon (i.e., providing additional tensile support for the tendon if the tendon is strained beyond expected normal recovery strain).

The second yarn and first yarn can overlap, interweaved or not, in a transition zone at the proximal end of the tendon. The third yarn and first yarn can overlap, interweaved or not, in a transition zone at the distal end of the tendon. When the graft is under tensile stress, the respective yarns can directly transfer tensile loads between the yarns in the transition zones or merely indirectly transfer loads (e.g., the first yarn can transfer a tensile load to the tendon without directly transferring the load to the second yarn, and the tendon can then transfer the tensile load to the second yarn).

The synthetic component can be intermingled throughout the biologic component by sewing (e.g., by a lockstitch or chain stitch), knitting, weaving, braiding, gluing, welding, ultrasonic welding, or combinations thereof. The synthetic component (e.g., yarn) can be inserted through the biologic component. The insertion can be done by a needle which pierces a substrate (i.e., the biological component). The synthetic component can transverse the biologic component non-parallel to the layers and/or surface of the biological component.

The graft can have tensile and/or compressive load sharing between the synthetic and biological components. The strength and compliance of the graft can be shared by the synthetic element and the biologic simultaneously. For example, the synthetic component may not stress shield the biological component and vice versa.

Most (e.g., greater than about 50%, or greater than about 75%, or greater than 90%) or all of the length of the synthetic component can be inside of the biological component, for example protected from abrasion by forces outside of the graft (e.g., rubbing against external tissue), and inflammatory or foreign body reaction by the in vivo environment outside of the biological component.

Figure 19A:
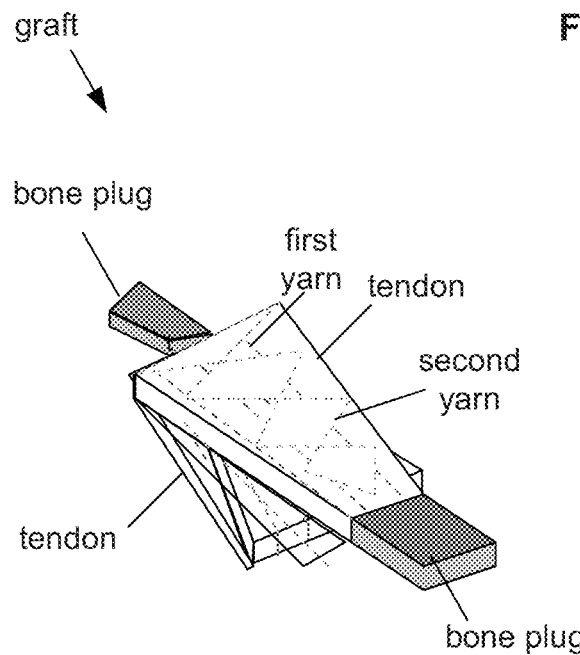
Figure 19B:
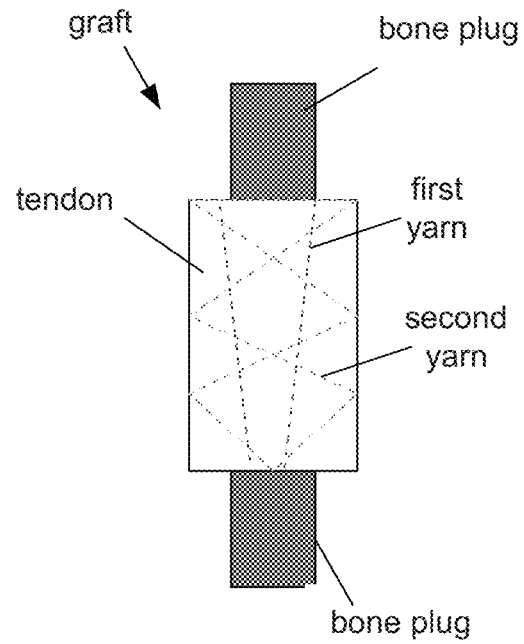

The synthetic component can hold or secure shapes and layers of the biological component together, for example to create complex 3-D composite shapes from biological components, such as shown in FIGS. 19a and 19b.

The synthetic components can partially or completely traverse the thickness or all or part of the biological component. The synthetic components can be stronger and/or stiffer than the biological components. The stitch pattern of the synthetic components and the intermingled nature of the synthetic with the biological components composite can allow the yarns to offload stress from the biological component and compress the biological component. A crimp interchange can allow the yarn filaments to move and provide relative compliance to match the biologic or backstop (retard elongation). A crimp interchange can have the stitch pattern as a spring, pulled axially. The boundaries of the "cells" of the crimp interchange can stretch and become two straight lines (i.e., the springs). The biological component tissue can be inside the "cells," for example, sharing, matching, and/or self-buffering the force load between the biological and synthetic components.

The graft can be from about 0% to about 100% synthetic component by volume, more narrowly from about 1% to about 20% synthetic component by volume, more narrowly from about 2% to about 10% synthetic component by volume.

The synthetic component can be used in only specific regions of the biologic component, such as only on the medial, or proximal, or distal, or lateral side of biologic component, or only in the transition zones and the adjacent hard and soft tissue, or combinations thereof.

The load forces applied to the biological component can smoothly (i.e., non-discretely) transition from the hard tissue to the soft tissue along the lengths of the transition zones. For example, the overlapping synthetic components can smoothly transfer the load between the first yarn and the second yarn in the transition zone. The first yarn can biodegrade over time (e.g., after 4 months) after implantation, for example, resisting tension, abrasion, and fatigue of the biological component until healing and re-strengthening of the biological component has substantially completed post-implant.

The graft can have a higher fracture toughness, mechanical strength, tensile strength (e.g., modulus of elasticity, yield, and failure strengths), shear strength, compression strength, torsion strength, and fatigue properties (e.g., hysteresis) than the respective unreinforced biological tissue (e.g., tendon and/or bone/hard tissue).

The synthetic component-reinforced hard tissue (e.g., bone) can have altered anisotropic properties, directional strength, modulus of elasticity, compliance, or combinations thereof compared with the respective unreinforced hard tissue. The hard tissue can be reinforced, for example, with single sewn thread systems (hand or machine sewn), fabric structures, larger cable like structures, other synthetic components described here, or combinations thereof. The synthetic components in the hard tissues can be made from polymers, metals, other materials disclosed herein, or combinations thereof.

Figure 3B:
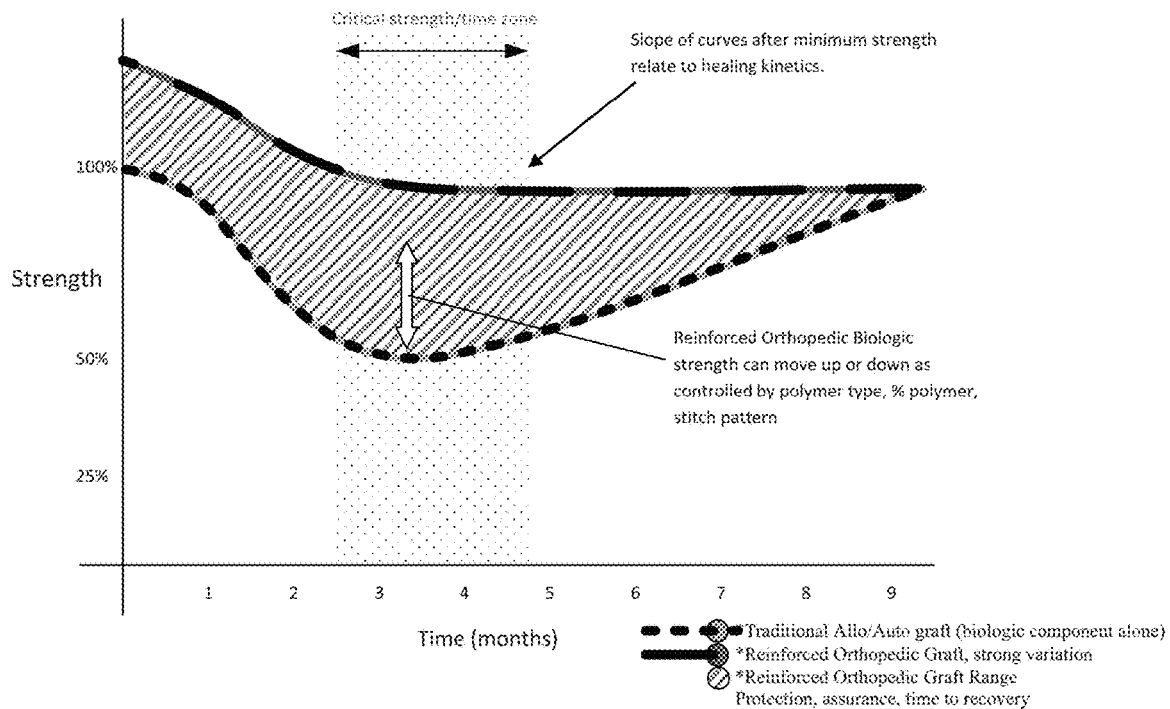
FIG. 3b is a strength vs. time graph of variations of the graft with a non-biodegradable synthetic component and an exemplary traditional biologic allograft or autograft graft.
Figure 3C:
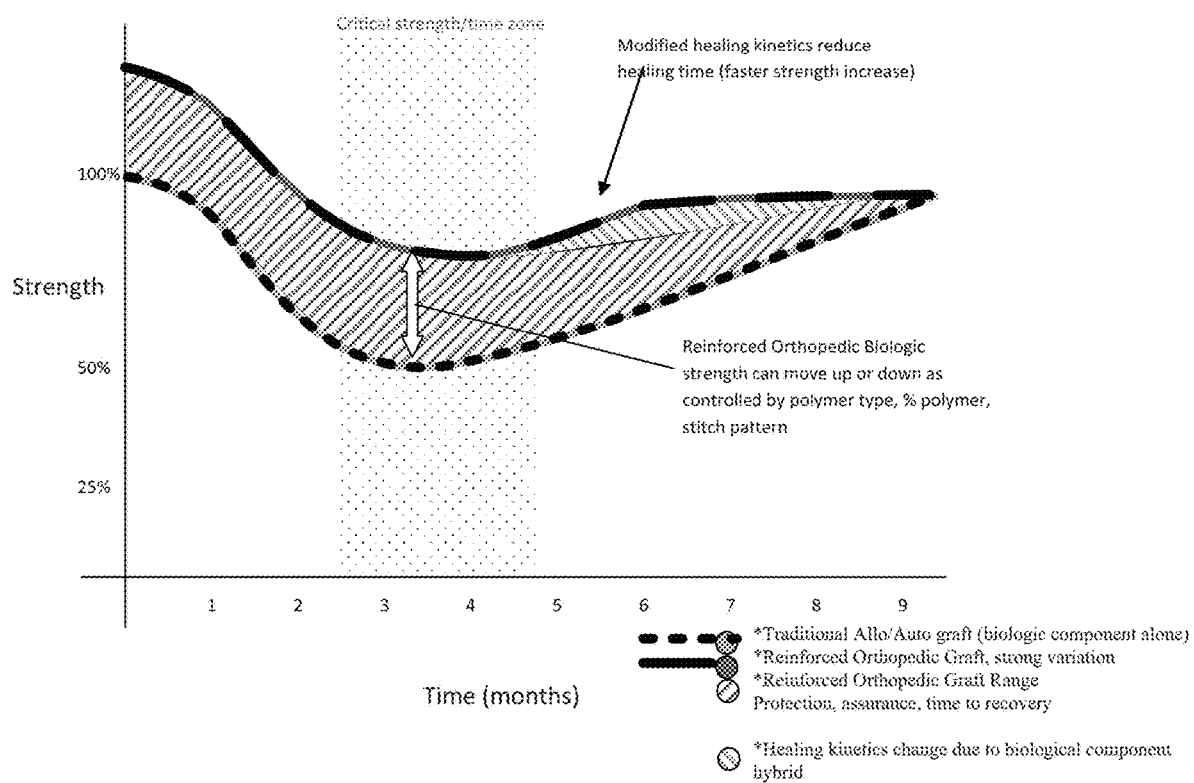
FIG. 3c is a strength vs. time graph of variations of the graft with a synthetic component and an exemplary traditional biologic allograft or autograft graft of tendon mixed with muscle tissue.

FIGS. 3a, 3b, and 3c illustrate strength curves of the graft variations over time after implantation. The loss of strength and compliance of a purely biological graft is known after a typical allograft or autograft is implanted in a patient. Tendons used as a biological component can lose up to 50% of their strength by the third month after implantation. The graphs illustrate exemplary composite mechanics of the present graft compared to a non-reinforced purely biological implant.

FIG. 3a is a strength vs. time graph of variations of the graft with a biodegradable synthetic component and an exemplary traditional biologic allograft or autograft graft.

FIG. 3b is a strength vs. time graph of variations of the graft with a non-biodegradable synthetic component and an exemplary traditional biologic allograft or autograft graft.

FIG. 3c is a strength vs. time graph of variations of the graft with a synthetic component and an exemplary traditional biologic allograft or autograft graft of tendon mixed with muscle tissue.

The graft performance of implanted strength over time can be have a negative slope (i.e., strength loss over time), positive slope (i.e., strength increase), or zero or flat slope (i.e., no strength change over time).

FIGS. 4a and 4b illustrate an Achilles tendon source tissue for the biological component. The biological component can have a bone plug at one end of the component. The tendon can be substantially trapezoidal with a narrow width at the end near the bone plug and a wider width at the end opposite the bone plug.

FIGS. 5a and 5b illustrate that the wider side corners of the tendon can be folded in opposite directions toward the longitudinal axis of the tendon, as shown by arrows, and sewn onto the remainder of the tendon.

Figure 6A:
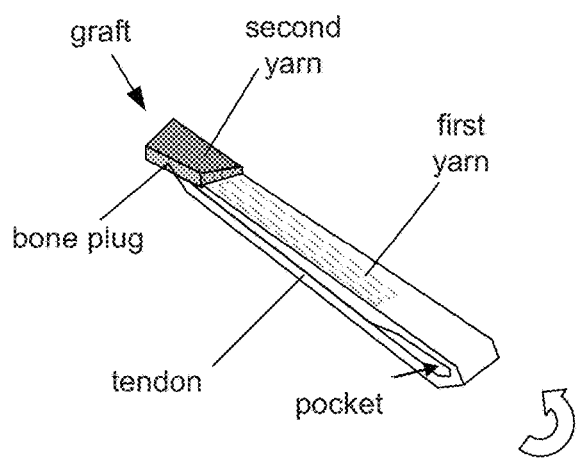
Figure 6B:
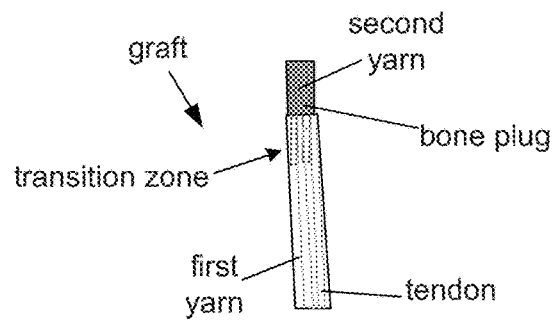

FIGS. 6a and 6b illustrate that the bone-less longitudinal end of the tendon can be rotated (e.g., flipped), as shown by arrow, around the longitudinal middle of the tendon and sewn to the other end of the tendon and/or the bone, for example with additional first or second yarn, and/or a third yarn. The crease of the fold can be an attachment pocket between the front length of the tendon and the back length of the tendon. A polymer ring or clasp (for example, that can be attached to tethers and/or one or more endobuttons) can be inserted through and be held by the attachment pocket. The front length of the tendon and the back length of the tendon can be left unsewn together along the pocket.

Figure 7A:
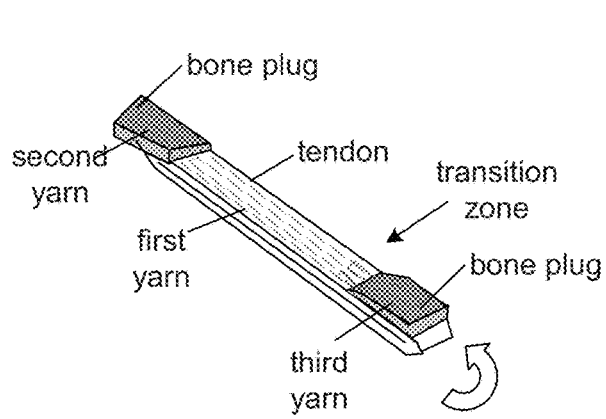
Figure 7B:
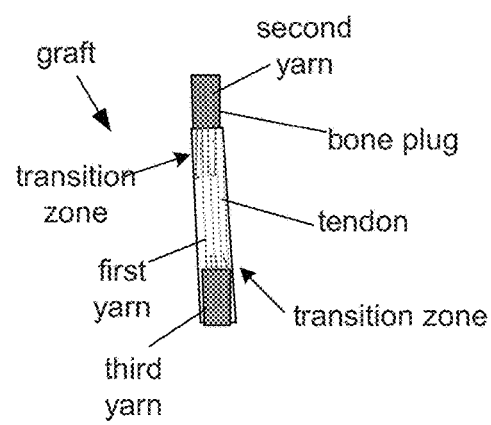

FIGS. 7a and 7b illustrate that the bone-less longitudinal end of the tendon can be rotated (e.g., flipped) again, as shown by arrow, around the longitudinal middle of the tendon and sewn to the other end of the tendon and/or the bone, as described in FIGS. 6a and 6b. A second bone plug can then be attached (e.g., sewn) onto the bone-less longitudinal end of the tendon with the third yarn.

The grafts shown herein can be implanted to a target site at any point or stage during the methods of making shown herein.

FIG. 8 illustrates that the graft can have interference bumps attached to the tendon. For example, the interference bumps can be sewn (e.g., with the first or second yarn) or adhered to the tendon. The first and second yarns can be longitudinally coincidental along the length of the tendon. The interference bumps can extend away from the tendon.

The tendon can be assembled from a number of layers of the same or different types of soft tissue that are sewn with one or more yarns or otherwise adhered together.

Multiple biologic components can be laminated or sewn together with the synthetic components. For example, a first layer of the graft can be a first biological component from a hamstring, a second layer of the graft can be a second biological component from the Achilles tendon, and a third layer of the graft can be a third biological component from the patellar tendon. The multiple biological components can have the same or different characteristics such as sidedness (e.g., rough or smooth), density, surface area (e.g., via papilla, ridges, holes, wrinkles, trabecular structure, or combinations thereof), layers of tissue for cell infiltration, holes for cell infiltration, biologic mechanical properties (e.g., strong or weak, stiff or elastic), porosity size and pore density, or combinations thereof.

The bone plugs can have cylindrical configurations with lateral slots or channels. The bone plugs can be translated or slid laterally, as shown by arrows, onto the tendon between the interference bumps. The bone plugs can then be sewn or adhered to the tendon (e.g., with the second yarn or third yarn). Excess length of tendon extending to the terminal ends of the tendon beyond the bone plug can be cut (e.g., past the interference bump on the terminal side of the bone plug) from the graft before implantation. Therefore, the graft length and bone plug location along the tendon can be adjusted by the surgeon after visualizing (directly or indirectly, such as through an artheroscope or MRI) and immediately before implantation, or after sizing by inserting and then withdrawing the graft and then further adjusting the graft length or bone plug position.

Pulling tethers can be attached to the bone plugs and/or the tendon. The pulling tethers can be various sizes, such as sized for small bore (e.g., soft tissue repair of the knee or shoulder), or large bore anchor systems (e.g., knee, hip, ankle, spine). The one or more pulling tethers can extend from the remainder of the device. The pulling tethers can be pulled on to translate the device through bone tunnels during placement of the device at the target site.

FIG. 9 illustrates that a terminal end of the tendon can be folded onto itself and sewed or adhered down upon itself to create a wider diameter than the remainder of the tendon at a fabricated interference. The bone plug can have a longitudinal channel or slot. The diameter of the longitudinal channel can be smaller than the diameter of the fabricated interference. The bone plug can be translated or slid, as shown by arrow, over the opposite end of the tendon from the fabricated interference.

FIG. 10 illustrates that the bone plug can be pushed onto the fabricated interference. The fabricated interference can have a fold crease from folding the tendon upon itself. A locking suture can be sewn tightly into or through the fabricated interference and through the fold crease, for example, to hold the fabricated interference in place. The bone plug can friction fit and/or interference fit on the fabricated interference and/or otherwise sewn or adhered to the tendon.

A second bone plug can be slid onto the tendon. A second fabricated interference can then be formed and the second bone plug can friction fit and/or interference fit on the second fabricated interference and/or otherwise sewn or adhered to the tendon.

Figures 11, 12:
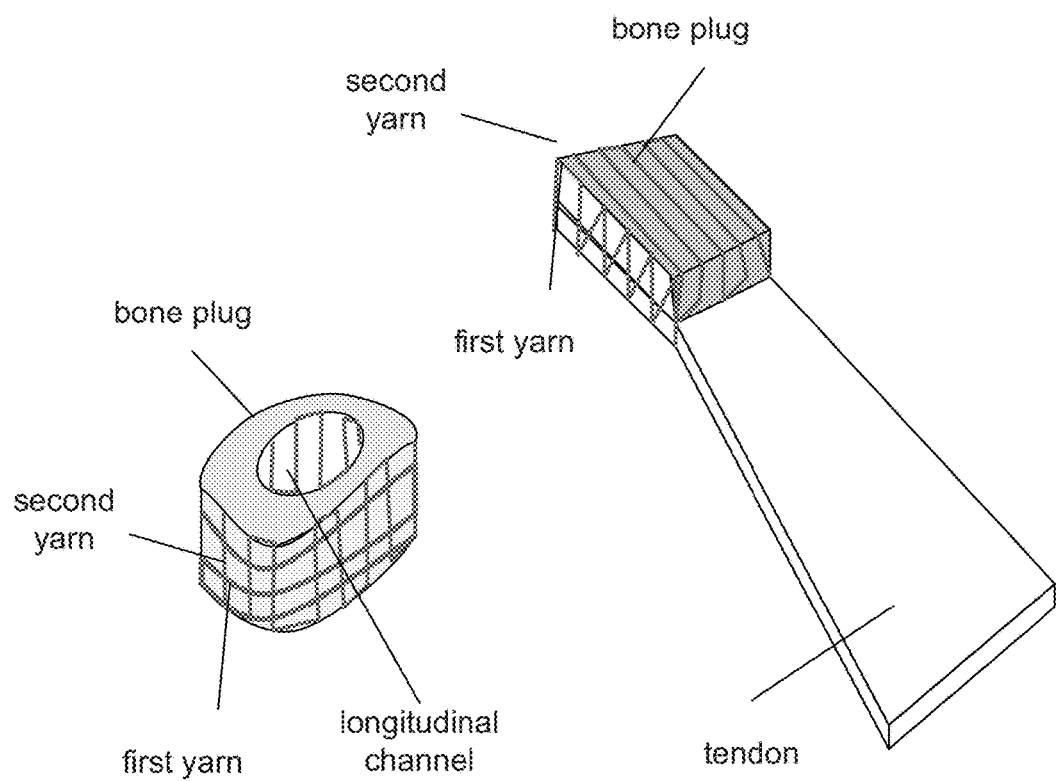
FIG. 11 is an isometric schematic view of a variation of the bone plug.
FIG. 12 is an isometric schematic view of a variation of the graft.

FIGS. 11 and 12 illustrate that the bone plugs can have first, second, and/or third yarns through the bone plugs in one or more directions. For example, the first yarn can intersect the second yarn crossing along radial coordinates in the bone plug as shown in FIG. 11. The first yarn can intersect the second yarn crossing perpendicularly or at a non-perpendicular angle along orthogonal coordinates in the bone plug as shown in FIG. 12. The first and second yarns can have different strengths, for example resulting in differing additional strength in different directions along the bone plug.

FIGS. 13a and 13b illustrate that multiple source biological components similar to the component shown in FIGS. 4a and 4b (e.g., Achilles tendon-sourced components) can be placed on top of each other in longitudinally opposite orientation. Similar to the method shown in FIGS. 5a and 5b, the wider side corners of the tendons can be folded toward the longitudinal axis of the tendon, as shown by arrows, but in the same direction, partially or completely enveloping, encapsulating, or encircling the opposite biological component, and sewn onto the remainder of the tendon and/or to the tendon and/or bone of the opposite biological component, as shown in FIGS. 14a and 14b. The first yard can extend parallel to the longitudinal axis of the graft. The second (or first) yarn can zig-zag back and forth across the graft at about 45° and about 135° angles to the longitudinal axis, crossing the first yarn that extends parallel to the longitudinal axis, further securing the first tendon to the second tendon.

Figure 15A:
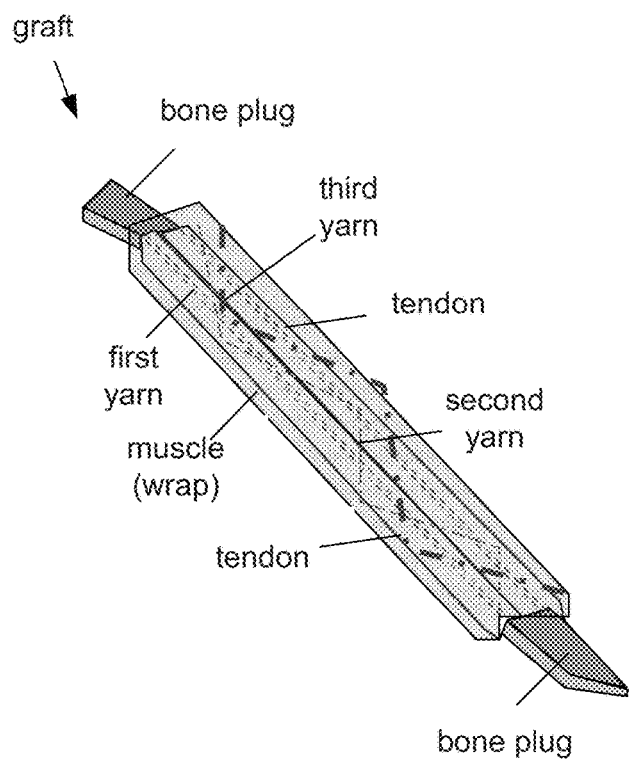
Figure 15B:
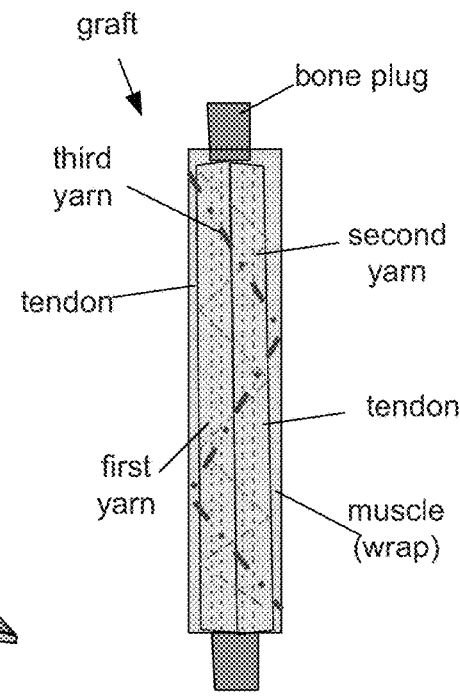

FIGS. 15a and 15b illustrate that the graft can be wrapped in another soft tissue component, such as tendon or muscle, or co-joined biologics such as tendon with muscle and/or ligament with muscle. The wrapping can partially or completely envelope, encapsulate, or encircle the soft and/or hard tissue of the remainder of the graft and can be attached to the remainder of the graft by adhering or sewing, for example with the third (and/or first and/or second) yarn zig-zagging at about 30° and about 150° angles to the longitudinal axis.

Figure 16:
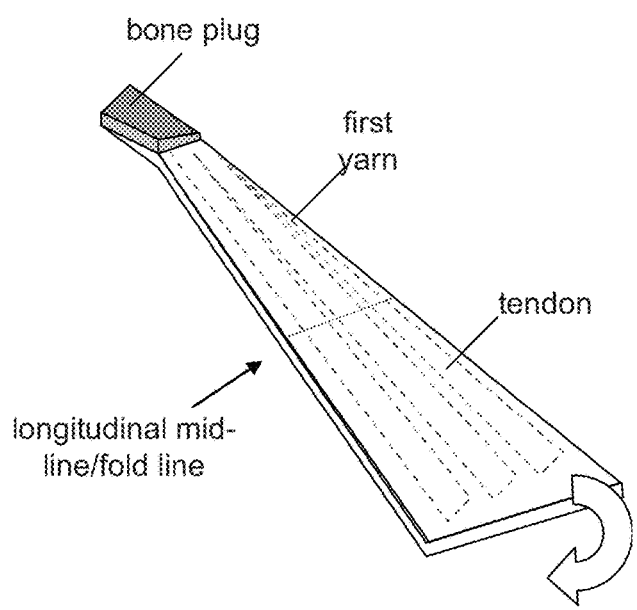
Figure 17:
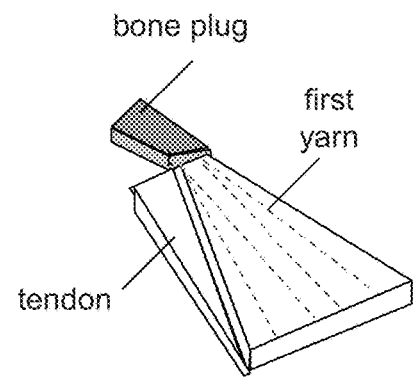

FIG. 16 illustrates a biological component similar to the component shown in FIGS. 4a and 4b (e.g., Achilles tendon-sourced components) that can have a first yarn sewn through the tendon. The bone-less longitudinal end of the tendon can be rotated (e.g., flipped), as shown by arrow, around the longitudinal mid-line of the tendon, as shown in FIG. 17. The free flap of the tendon can be sewn to the other end of the tendon and/or the bone, for example with additional first or second yarn.

Figure 18:
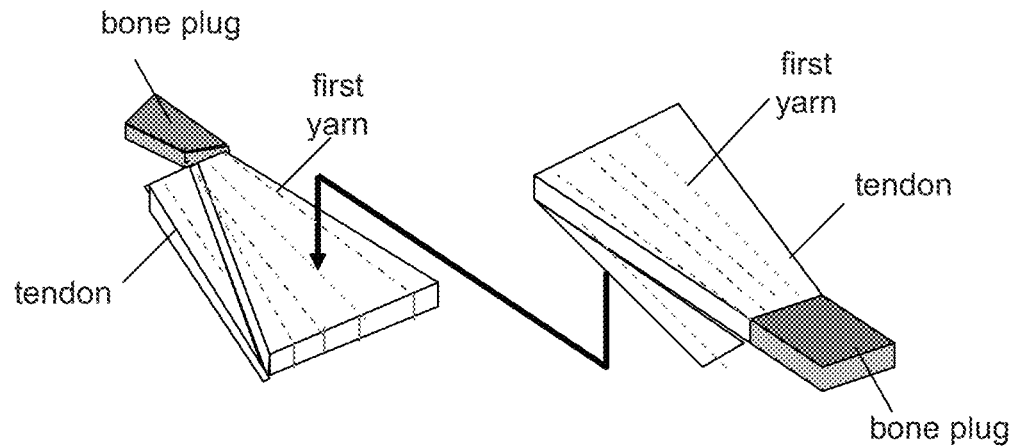

FIG. 18 illustrates that the method shown in FIGS. 16 and 17 can be performed on two biological components/grafts. The biological components/grafts can be oriented longitudinally opposite to each other and then brought into contact with each other into an assembly as shown by arrow.

FIGS. 19a and 19b illustrates that the assembly of FIG. 18 can then be secured together with adhesive and/or second (and third, if desired) yarn stitched through the tendons of both biological components. The resulting graft can have four layers of tendons (i.e., each of two biological component tendons folded over onto itself).

Other tendons in the body that can be soft tissue, for example as layers and sewn together, include the iliofemoral ligament, hamstring, sartorius, thoracolumbar facia (thin wide sheets of tendon), or combinations thereof.

The assembled biological devices can have the bone anchors pre-attached or attached and installed during surgery. The bone anchors can lock on to the remainder of the device by an interference fit of be sutured in place. The bone anchors can be external to the soft tissue or embedded inside the soft tissue element.

The biological tissue component or element can be 100% soft tissue or have a single or more than one hard tissue (e.g., bone) element. The hard tissue elements can be harvested pre-attached or post sewn in place.

The reinforced graft can have a secondary tissue source, thereby being a Hybrid Biologic Device (HBD), as shown in FIGS. 13a through 15b and 18 through 19b. The HBD can source biological components from tissue that are complimentary in characteristics, such as a higher strength tissue combined with a tissue with faster healing kinetics. For example, less dense by weight (g/cc) tissue, more open (i.e., porous) tissue, and less inflammatory tissue can be used with similar tissue and/or with tissue with more strength but a higher density and less porous. HBD tissue can include combinations of muscle tissue, peritoneum, rumen, stomach, urinary bladder, liver, human dermis, fetal bovine dermis (e.g., as less strong but faster healing) with other similar tissue or with higher strength biological source tissue mentioned elsewhere herein. The HBD could also be a combination of textile or film structure. For example a weave of warp knitted structure or degrading (e.g., biodegradable) or non-degrading (e.g., non-biodegradable) material. The textile or film can be secured to a biologic component with sewing as illustrated herein.

Figures 20, 21:
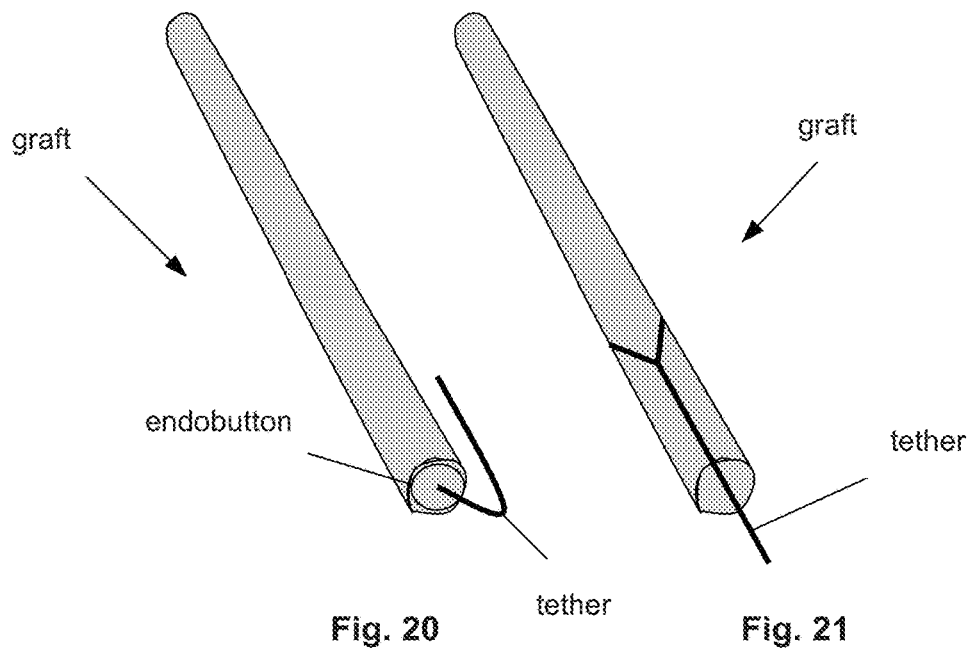
FIGS. 20 through 22 illustrate schematic variations of the graft.

FIG. 20 illustrates that the graft can have a tether sewn into the graft and extending from the terminal end of the remainder of the graft. The tethers can be used to pull the graft into a target site, such as a bone tunnel. The tether can extend from the radial center or radial edge of the graft.

The device can have one or more endobutton fixation elements. For example, the endobuttons can attach to the tethers and rest, press, or be separately fixed (e.g., with bone screws) against the outer cortical surface of the bone on the outside of the bone tunnels. The endobuttons can be attached to the tethers like a The endobuttons can be wider than the bone tunnel. The endobutton can fix the device at the target site by preventing or minimizing translation away from the endobutton.

FIG. 21 illustrates that the tether can extend from the radially outer surface of the graft at one or more points, such as encircling the graft and attaching by adhering to or weaving through along part or all of the outer circumference. The tether can be sewn deeper into the graft.

Figures 22, 23:
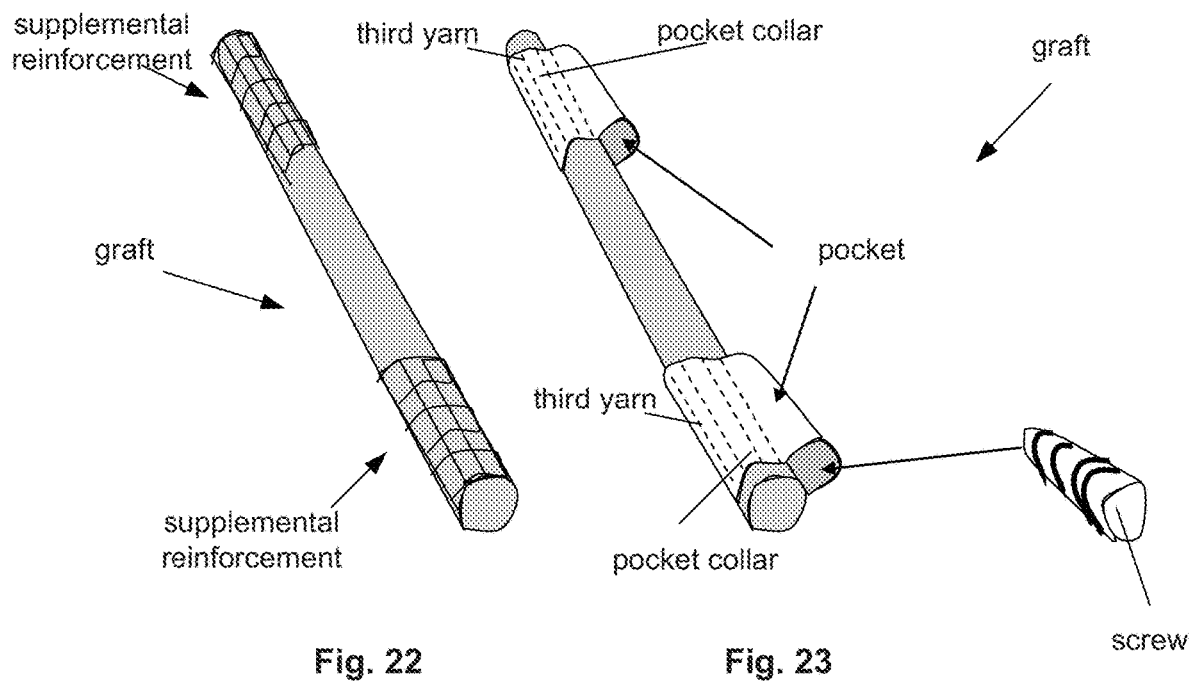
FIGS. 23 and 24 schematically illustrate variations of methods for using variations of the graft with a friction-fit screw.

FIG. 22 illustrates that one or both of the opposite longitudinal ends of the graft can have supplemental reinforcements, such as meshes or screens. The supplemental reinforcements can have additional yarn, higher stitch densities, larger diameter yarn, stronger material yarn, or combinations thereof, than the remainder of the graft. For example, tethers can be attached to the supplemental reinforcements. A static or expanding screw can be inserted into or radially adjacent to the length of the supplemental reinforcement to friction fit the graft into the target site.

The sewn reinforcement, such as the supplemental reinforcement or any of the synthetic components, can bolster proximal and distal implant anchoring zones in the graft. A soft tissue implant can be developed to behave and be anchored like a bone tendon bone. The supplemental reinforcement can increase the stitch density at the implant end sections, for example by adding additional structures to the biologic component such as open pore textile structures and tethers (e.g., lines, cords, sutures, or combinations thereof).

FIG. 23 illustrates that the graft can have pocket collars attached to one or both of the opposite longitudinal ends of the graft. The pocket collars can be made from macro pore fabric, any other material disclosed herein, or combinations thereof. The pocket collars can be attached to the remainder of the graft, for example by stitching the collar to the remainder of the graft with the third (and/or first and/or second) yarn. The pocket collars can have hollow pockets extending laterally away from the graft. When the graft is at the target site, one or more friction fit screws can be inserted into the pockets, as shown by arrow, to friction fit the graft into the target site.

Figure 24:
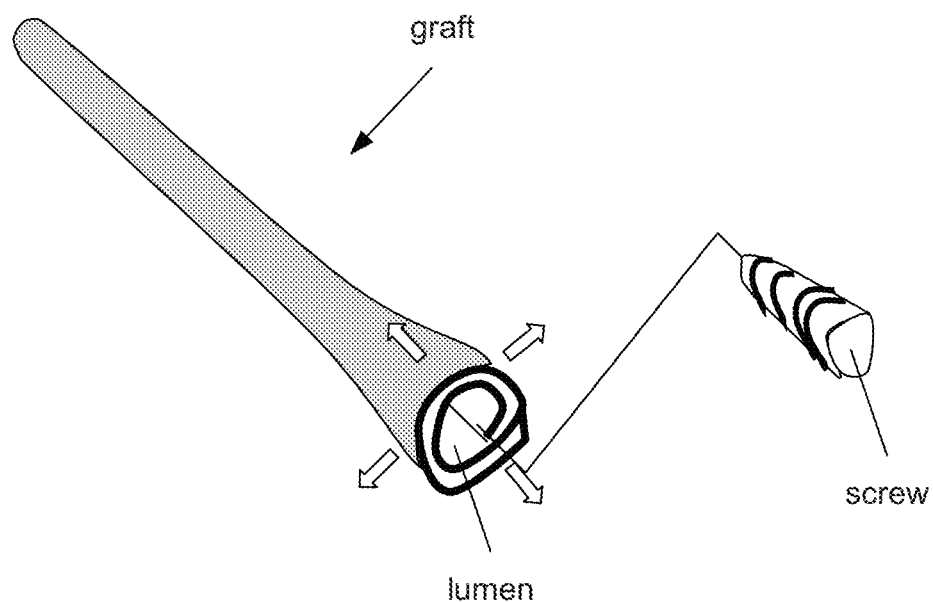

FIG. 24 illustrates that the graft can have a hollow lumen through the entire length of graft or only at one or both terminal ends. The lumen can be radially central and collinear with the longitudinal axis or radially offset. A guidewire can be deployed through the lumen, for example, to deliver the graft to the target site. The lumen can also form a pocket to receive a screw. A static or radially expanding screw, such as a bone screw, can be inserted into the lumen to expand the graft, as shown by arrows, and friction fit the graft into the target site.

The graft shown in FIG. 24 can be made by rolling any of the flat variations described herein. For example, the bone plug ends can be shaped to accept a smaller screw. The bone plug can be cut into four quarters. The screw can be pushed through the middle of the bone plug quarters causing the plug quarters to expand. The bone plug can be tapered proximal to distal. As the screw is screwed in, the screw can push the bone plug deeper radially into the bone tunnel wall of the target site.

Figures 25A, 25B:
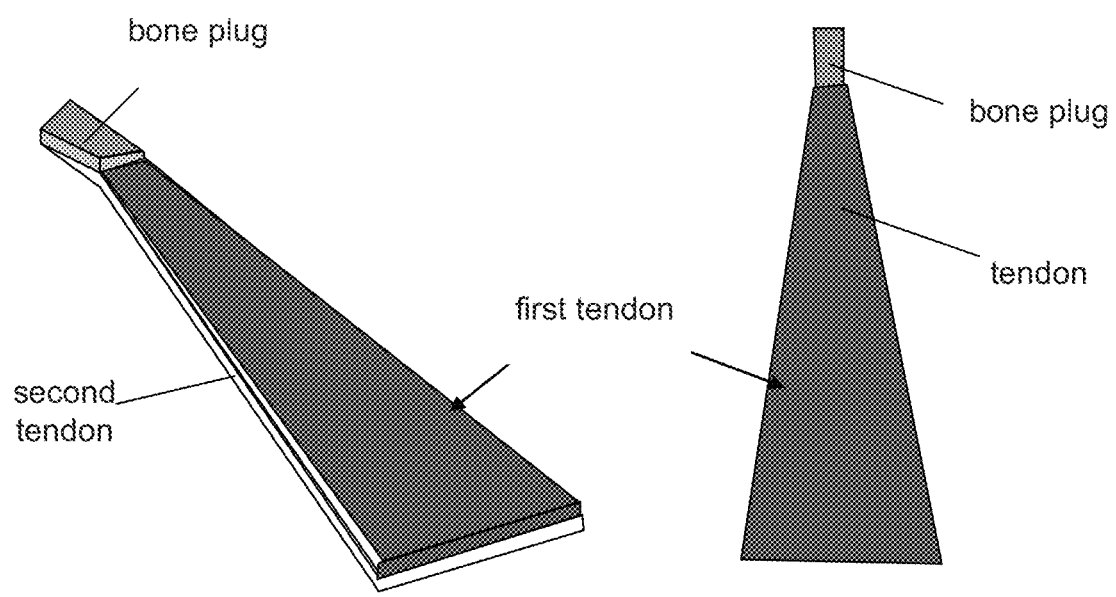

FIGS. 25a and 25b illustrate a biological component similar to the component shown in FIGS. 4a and 4b (e.g., Achilles tendon-sourced components) that can have a first tendon and a second tendon directly in contact with each other, approximately the same size and shape, and aligned with each other.

Figures 26A, 26B:
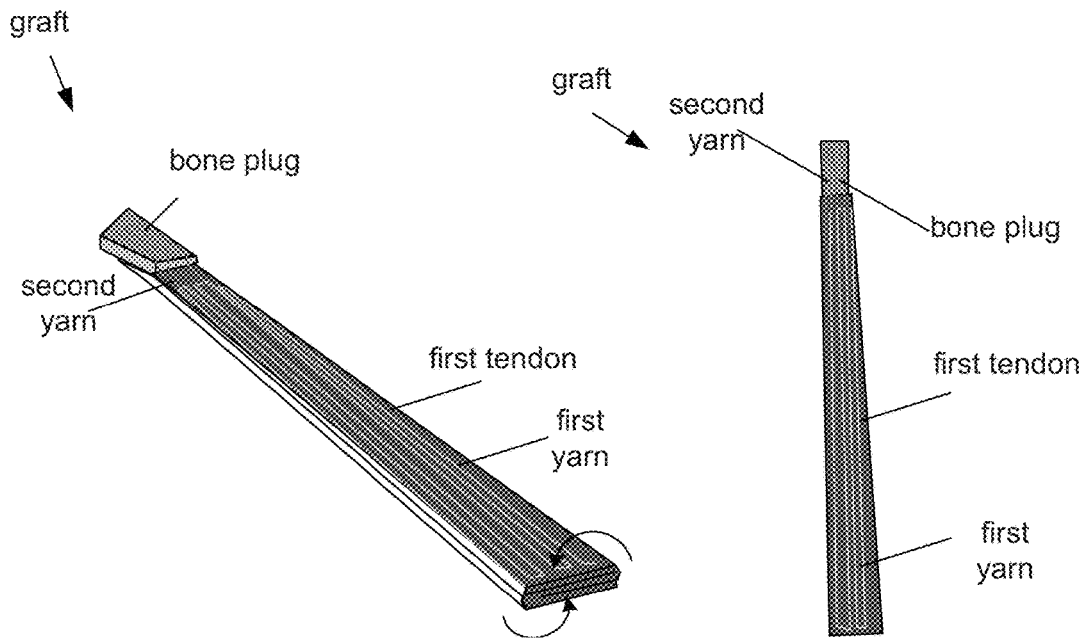

FIGS. 26a and 26b illustrate that the wider side corners of the first and second tendons can be folded in opposite directions toward the longitudinal axis of the tendon, as shown by arrows, and sewn onto the remainder of the tendons.

Figures 27, 28, 29:
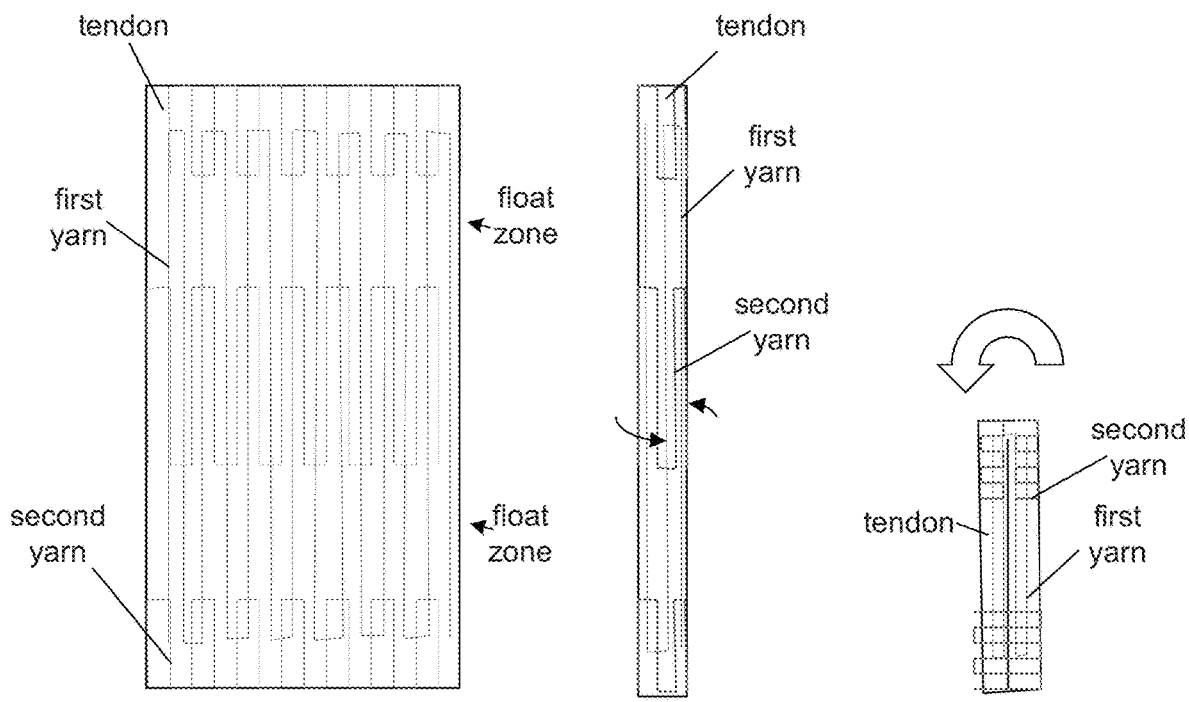
FIGS. 27 through 29 schematically illustrate a variation a method for making the graft.

FIG. 27 illustrates that the second yarn can, for example, secure any additional soft tissue layers together. The first yarn can, for example, supplement the axial strength of the graft, for example during the healing stage. The first yarn can form a lockstitch with the second yarn. The top and bottom yarns in the lockstitch can have the same or different materials, diameters, filament quantity (e.g., monofilament or multifilament), biodegradability (e.g., capable of biodegrading at all and the rate of degradation), or combinations thereof.

The graft can have a float zone where the second yarn is absent. The float zone can be an area where the stitch of the second yarn (or respective yarn of the particular float zone) skips an additional distance and "floats," for example outside of the biological component, to a location outside of the float zone where the regular stitch pattern resumes. The float zone can have a reduced stitch density relative to the non-float zones. The float zones can have reduced stiffness and higher flexibility than the remainder of the device.

FIG. 28 illustrates that the graft can be rolled, as shown by arrows, into a cylinder.

FIG. 29 illustrates that the graft can be folded over, as shown by arrow, around the longitudinal mid-point.

Yarns or threads can be sewn in strength lines for axial strength.

Threads can be sewn in, for example, straight, zig zag, or saw tooth patterns for securing layers together.

When systems of biologic components are sewn together, the larger diameter filaments can be hidden inside the final part. For example two layers of biologic material can be sewn together, 4/0 suture top surface, 2/0 bottom surface. The structure can be rolled so the 2/0 suture are oriented toward the inside of the cylindrical roll. (4/0 and 2/0 refer to exemplary USP suture sizes.)

Larger and/or high density yarns than the rest of the yarns can be used in some locations along the surface of the graft, for example, to increase the roughness of the surface texture and friction between the graft and surrounding tissue, and anchor (e.g., friction fit screw) engagement against the graft.

The synthetic components can have a stitch density, stitch length, stitch pattern and filament size.

Exemplary combinations of elements and characteristics for non-limiting variations of the graft include:

The graft can have a hamstring tendon (such as FIGS. 4a and 4b without a bone plug), with no bone plug as the biological component or orthobiologic structure sewn with a 0 UHMWPE braided suture (i.e., yarn). The graft can have six straight sew lines of the suture using a lockstitch pattern white thread with a 5 mm stitch length. The suture can penetrate the hamstring tendon. The graft can have two hamstring tendons. The two tendons combined folded in half (e.g., stacked) and then sewn together using a 2/0 black UHMWPE braided suture in either straight lines of diamond pattern. The graft can have a 5 mm stitch length lock stitch The graft can have soft tissue tendonous facia with no bone plug, similar to FIGS. 27 through 29 as the biological component or orthobiologic structure sewn with a first yarn of 0 UHMWPE braided suture. A second yarn threads can be 0 UHMWPE and be braided sutures sewn into the high stress regions, such as transitions zones. The graft can have 12 straight sew lines using a lock stitch pattern for the first yarn with a 5 mm stitch length. The suture can penetrate the facia sheet. (Wider, thinner soft tissue can have 12 stitch lines spaced further apart than above.) The sheet can then be rolled, folded in half (i.e., stacked) and then sewn together using a 2/0 black UHMWPE braided suture in either straight lines or a diamond pattern using a 5 mm stitch length lock stitch or a surgeon whip stitch.

The graft can have soft tissue Achilles tendon with a bone plug, such as FIGS. 4a and 4b, the biological component or orthobiologic structure sewn with a 0 UHMWPE braided suture as the first yarn. The graft can have 12 sew lines (e.g., fanning shape, narrow at bone tendon interface) using a lock stitch pattern white thread with a 5 mm stitch length. The suture can penetrate the tendon. The tendon can be folded in thirds (stacked) and then sewn together using a 2/0 black UHMWPE braided suture in either straight lines of diamond pattern with a 5 mm stitch length lock stitch. The tendon can then be folded in half length-wise and then sewn together using a 2/0 black UHMWPE braided suture in either straight lines of diamond pattern with a 5 mm stitch length lock stitch.

The biological component or orthobiologic structure can be two Achilles tendons with bone plugs as sewn with a 2/0 UHMWPE braided suture as the first yarn. The graft can have 12 sew lines (fanning shape, narrow at bone tendon interface) using a lock stitch pattern white thread with a 5 mm stitch length for the first yarn. The suture can penetrate the tendon. Two of these structures can be made and combined to make final graft. The tendons can be folded in half and then sewn together using a 2/0 black UHMWPE braided suture in either straight lines of diamond pattern using a 5 mm stitch length lock stitch.

Any of the above devices can have fabric attached to the ends of the device, similar to that shown in FIG. 23. The fabric can be a pre-shaped warp knitted mesh tube made from any of the materials herein, such as Polypropylene or UHMWPE polymers. Warp knit fabric can have an weight density per coverage area of about 70 g/cm^2 and an average pore size of about 2 mm.

Any or all elements of the synthetic components and/or other devices or apparatuses described herein (including other non-biological elements of the graft) can be made from, for example, a single or multiple stainless steel alloys, nickel titanium alloys (e.g., Nitinol), cobalt-chrome alloys (e.g., ELGILOY® from Elgin Specialty Metals, Elgin, IL; CONICHROME® from Carpenter Metals Corp., Wyomissing, PA), nickel-cobalt alloys (e.g., MP35N® from Magellan Industrial Trading Company, Inc., Westport, CT), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, DE), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, NJ, or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, MA), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudopolyamino tyrosine-based acids, extruded collagen, silicone, zinc, echogenic, radioactive, radiopaque materials, any of the other materials listed herein or combinations thereof. Examples of radiopaque materials are barium sulfate, zinc oxide, titanium, stainless steel, nickel-titanium alloys, tantalum and gold.

The synthetic components of the device can be made from substantially 100% PEEK, substantially 100% titanium or titanium alloy, or combinations thereof.

The synthetic (and biological) elements described herein can be made (at least) in part from a biomaterial (e.g., cadaver tissue, collagen, allograft, autograft, xenograft, bone cement, morselized bone, osteogenic powder, beads of bone).

Any or all elements of the device and/or other devices or apparatuses described herein, can be, have, and/or be completely or partially coated with agents for cell ingrowth.

The device and/or elements of the device and/or other devices or apparatuses described herein can be filled, coated, layered and/or otherwise made with and/or from cements, fillers, and/or glues known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, PA; indomethacin; mefenamic acid), COX-2 inhibitors (e.g., VIOXX® from Merck & Co., Inc., Whitehouse Station, NJ; CELEBREX® from Pharmacia Corp., Peapack, NJ; COX-1 inhibitors); immunosuppressive agents, for example Sirolimus (RAPAMUNE®, from Wyeth, Collegeville, PA), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin E2 Synthesis in Abdominal Aortic Aneurysms, Circulation, Jul. 6, 1999, 48-54; Tambiah et al, Provocation of Experimental Aortic Inflammation Mediators and *Chlamydia Pneumoniae*, Brit. J. Surgery 88 (7), 935-940; Franklin et al, Uptake of Tetracycline by Aortic Aneurysm Wall and Its Effect on Inflammation and Proteolysis, Brit. J. Surgery 86 (6), 771-775; Xu et al, Spl Increases Expression of Cyclooxygenase-2 in Hypoxic Vascular Endothelium, J. Biological Chemistry 275 (32) 24583-24589; and Pyo et al, Targeted Gene Disruption of Matrix Metalloproteinase-9 (Gelatinase B) Suppresses Development of Experimental Abdominal Aortic Aneurysms, J. Clinical Investigation 105 (11), 1641-1649 which are all incorporated by reference in their entireties.

Bone plugs as shown herein can be bone pieces, wedges, struts, cortical bone, cancellous bone, composites of cortical and cancellous bone, or combinations thereof.

Any elements described herein as singular can be pluralized (i.e., anything described as "one" can be more than one). Any species element of a genus element can have the characteristics or elements of any other species element of that genus. (e.g., "Tendon" is used as an exemplary soft tissue throughout the disclosure, but can be any soft tissue or combinations thereof. "Yarn" is used as an exemplary synthetic component throughout the disclosure but can be any synthetic component or combinations thereof.) The above-described configurations, elements or complete assemblies and methods and their elements for carrying out the invention, and variations of aspects of the invention can be combined and modified with each other in any combination.

We claim:

1. An implantable orthopedic device for implantation as a tensile load bearing element in a target site comprising:
    a biological component comprising a soft tissue and a hard tissue;
    a first synthetic component configured to sustain a first portion of a tensile load; and
    a second synthetic component configured to sustain a second portion of the tensile load,
    wherein the second synthetic component extends in multiple directions through the soft tissue and through the hard tissue,
    wherein the hard tissue has a hard tissue length, a hard tissue width, and a hard tissue height, wherein the hard tissue length is greater than the hard tissue width and the hard tissue height,
    wherein the soft tissue has a soft tissue length, a soft tissue width, and a soft tissue height, wherein the soft tissue length is greater than the soft tissue width and the soft tissue height,
    wherein the second synthetic component extends through the hard tissue along the hard tissue length and through the soft tissue along the soft tissue length,
    wherein the hard tissue comprises a hard tissue first channel and a hard tissue second channel, wherein the hard tissue first channel is the same distance from a longitudinal center of the biological component as the hard tissue second channel,
    wherein the hard tissue first channel has multiple turns, and wherein the second synthetic component extends along the multiple turns.

2. The implantable orthopedic device of claim 1,
    wherein the biological component has a longitudinal axis that extends along the soft tissue and the hard tissue,
    wherein the first synthetic component is configured to sustain the first portion of the tensile load along the longitudinal axis, wherein the first synthetic component extends through the soft tissue along the longitudinal axis, and
    wherein the second synthetic component is configured to sustain the second portion of the tensile load along the longitudinal axis, wherein the second synthetic component extends through the soft tissue and the hard tissue along the longitudinal axis.

3. The implantable orthopedic device of claim 1, wherein the second synthetic component extends through the soft tissue and the hard tissue such that the second synthetic component sequentially extends from the hard tissue, into the soft tissue, and then back into the hard tissue.

4. The implantable orthopedic device of claim 1, wherein the second synthetic component is stitched through the soft tissue and the hard tissue.

5. The implantable orthopedic device of claim 1, wherein a total length of the first synthetic component is greater than the soft tissue length, and wherein a total length of the second synthetic component is greater than the hard tissue length.

6. The implantable orthopedic device of claim 1, wherein a total length of the first synthetic component is greater than the hard tissue length, and wherein a total length of the second synthetic component is greater than the hard tissue length.

7. The implantable orthopedic device of claim 1, wherein a total length of the first synthetic component is greater than a total length of the biological component, and wherein a total length of the second synthetic component is greater than the hard tissue length.

8. The implantable orthopedic device of claim 1, wherein the second synthetic component overlaps with the first synthetic component.

9. The implantable orthopedic device of claim 1, wherein the soft tissue comprises at least one of a ligament, a tendon, and a muscle.

10. The implantable orthopedic device of claim 1, wherein the hard tissue comprises a first bone plug at a first end of the device and a second bone plug at a second end of the device.

11. The implantable orthopedic device of claim 1,
    wherein the hard tissue has a hard tissue first longitudinal terminal end and a hard tissue second longitudinal terminal end,
    wherein the soft tissue has a soft tissue first longitudinal end, a soft tissue second longitudinal end, and a soft tissue longitudinal center between the soft tissue first longitudinal end and the soft tissue second longitudinal end,
    wherein the hard tissue first longitudinal terminal end and the hard tissue second longitudinal terminal end are closer to the soft tissue first longitudinal end than to the soft tissue longitudinal center,
    wherein the hard tissue first longitudinal terminal end is closer to the soft tissue longitudinal center than the hard tissue second longitudinal terminal end,
    wherein a first portion of the second synthetic component is between the hard tissue first longitudinal terminal end and the hard tissue second longitudinal terminal end, and
    wherein a second portion of the second synthetic component is between the hard tissue first longitudinal terminal end and the soft tissue longitudinal center.

12. The implantable orthopedic device of claim 11, wherein the first synthetic component overlaps with the second synthetic component in the soft tissue.

13. The implantable orthopedic device of claim 11, wherein the first synthetic component extends across the second synthetic component in the soft tissue.

14. The implantable orthopedic device of claim 11, wherein a length of the second synthetic component is greater than the soft tissue length.

15. The implantable orthopedic device of claim 11, wherein a length of the second synthetic component is greater than the hard tissue length, and wherein the length of the second synthetic component is greater than the soft tissue length.

16. The implantable orthopedic device of claim 11, wherein a total length of the second synthetic component is greater than the hard tissue length as measured from the hard tissue first longitudinal terminal end to the hard tissue second longitudinal terminal end.

17. The implantable orthopedic device of claim 1, wherein the first synthetic component extends in multiple directions back and forth from a biological component first lateral side to a biological component second lateral side, and wherein the first synthetic component extends through the soft tissue along the soft tissue length.

18. The implantable orthopedic device of claim 1, wherein a length of the second synthetic component in the hard tissue first channel is greater than a length of the hard tissue.

19. The implantable orthopedic device of claim 1, wherein the implantable orthopedic device has a first longitudinal end and a second longitudinal end opposite the first longitudinal end, wherein the first longitudinal end comprises the hard tissue, and wherein the second longitudinal end comprises the soft tissue.

20. The implantable orthopedic device of claim 19, wherein the first longitudinal end further comprises the soft tissue.

21. The implantable orthopedic device of claim 1, wherein the first synthetic component extends through the soft tissue along the soft tissue length.

\* \* \* \* \*